United States Patent [19]

Cimini

[11] Patent Number: 5,022,417
[45] Date of Patent: Jun. 11, 1991

[54] INDIVIDUALIZED FLOSSING MOUTHPIECE ASSEMBLY AND METHOD OF PREPARING AND USING SAME

[76] Inventor: Peter D. Cimini, 120 Northwood Rd., Newington, Conn. 06111

[21] Appl. No.: 529,469

[22] Filed: May 29, 1990

[51] Int. Cl.$^5$ ............................................. A61C 15/00
[52] U.S. Cl. ................................................. 132/323
[58] Field of Search ............... 132/323, 324, 325–327; 433/6; 128/861

[56] References Cited

U.S. PATENT DOCUMENTS

| | | | |
|---|---|---|---|
| 3,311,977 | 4/1967 | Drake | 433/6 |
| 3,319,626 | 5/1967 | Lindsay | 433/6 |
| 4,350,154 | 9/1982 | Feldbau | 128/861 |
| 4,440,184 | 4/1984 | Smith | 132/323 |
| 4,460,002 | 7/1984 | Burdette, Jr. | 132/323 |
| 4,505,672 | 3/1985 | Kurz | 433/6 |
| 4,531,530 | 7/1985 | Aiken | 132/323 |
| 4,657,033 | 4/1987 | Dalton | 132/323 |
| 4,729,392 | 3/1988 | Tenny | 132/323 |

FOREIGN PATENT DOCUMENTS 2923057  12/1980  Fed. Rep. of Germany ...... 132/323

Primary Examiner—Gene Mancene
Assistant Examiner—Michael Lynch
Attorney, Agent, or Firm—CTC & Associates

[57] ABSTRACT

An individualizable flossing mouthpiece for simultaneously flossing a plurality of spaces between adjacent pairs of a person's teeth is a channel shaped member with an outer wall portion, and inner wall portion having free edges and a gap therebetween. The mouthpiece can receive a set of teeth in the gap. The wall portions have outer and inner series of closely spaced slots to receive dental floss therein. The distance between adjacent ones of the slots is less than the average tooth width, and dental floss can be impositively trapped in selected ones of the slots. The material of the channel shaped member is such that it can receive and permanently retain markings identifying certain ones of the slots in the outer wall portion. The mouthpiece can be individualized by placing the same in the person's mouth with the person's teeth in the gap and identifying those slots (less than all) in the outer wall portion corresponding to the edges of the person's teeth. An individualized flossing mouthpiece assembly adds dental floss to the individualized flossing mouthpiece, the floss extending through each so identified slot and across the gap to and through the corresponding slot in the inner wall portion. The individualized assembly is used by placing same in the person's mouth with the pre-placed floss between the person's teeth and moving the mouthpiece.

18 Claims, 1 Drawing Sheet ns and method of preparing and
using same

BACKGROUND OF THE INVENTION

The present invention relates generally to oral hygiene and more particularly to flossing and still more particularly to an individualizable flossing mouthpiece and to an individualized flossing mouthpiece and to an individualized flossing mouthpiece assembly for simultaneously flossing a plurality of spaces between adjacent pairs of teeth, either upper or lower. The invention also relates to a method of preparing an individualized flossing mouthpiece assembly and to a method of simultaneously flossing a plurality of spaces between a person's teeth using the individualized flossing mouthpiece assembly.

The benefits of flossing are well known and are becoming even better known. The present invention facilitates flossing by enabling all upper teeth to be flossed simultaneously and all lower teeth to be flossed simultaneously.

Furthermore, the invention enables all upper teeth or all lower teeth to be flossed simultaneously in a manner that is both simple and inexpensive.

In addition, the inventive flossing mouthpiece is readily individualized for flossing the upper teeth or the lower teeth of a particular person.

A patentability search hereon revealed the following U.S. Pat. Nos.:

| U.S. Pat. No. | Date | Inventor |
| --- | --- | --- |
| 4,440,184 | April 3, 1984 | Smith |
| 4,460,002 | July 17, 1984 | Burdette, Jr. |
| 4,531,530 | July 30, 1985 | Aiken |
| 4,657,033 | April 14, 1987 | Dalton |
| 4,729,392 | March 8, 1988 | Tenny |

The aforesaid prior patents are believed to have no detrimental effect on the patentability of the present invention, at least for the reason that they do not address or offer any solution to the problem of simultaneously flossing a plurality of spaces between adjacent pairs of teeth.

Important objects of the present invention are to provide an individualizable flossing mouthpiece and an individualized flossing mouthpiece assembly that attains the foregoing objects and advantages.

Other important objects of the present invention are to provide a method of preparing an individualized flossing mouthpiece and a method of using an individualized flossing mouthpiece, both methods being simple and inexpensive.

The manner in which the invention attains the foregoing objects and advantages will appear hereinafter.

SUMMARY OF THE INVENTION

An individualizable flossing mouthpiece for use in simultaneously flossing a plurality of spaces between adjacent pairs of teeth is provided by a channel shaped member including an outer wall portion, an inner wall portion and a web portion joining the wall portions. The wall portions have a gap therebetween and extend from the web portion to free edges and are curved in plan view. The mouthpiece is sized and shaped to receive a set of teeth loosely in the gap. The outer wall portion and the inner wall portion are provided respectively with outer and inner series of identical closely spaced slots which are adapted to receive dental floss therein. Each slot of the outer series has an open end in open communication with the free edge of the outer wall portion and each slot of the inner series has an open end in open communication with the free edge of the inner wall portion. The distance between adjacent ones of the slots of the outer and inner series is less than the width of an average tooth.

The wall portions are arcuate, such that said mouthpiece is generally C-shaped in plan view, and the channel shaped member has open ends facing generally in the same direction.

Each slot has a V-shaped portion providing the open end of the slot and widest thereat and narrowest at a location remote from the open end. Each slot also has a closed portion in open communication with the V-shaped portion at its narrowest location. The closed portion of each slot is generally cylindrical and is offset from a plane of symmetry of its associated V-shaped portion, thus providing a constricted portion joining the V-shaped portion and the closed portion.

Dental floss introduced into the V-shaped portion of any said slot can be moved therein to and beyond the constricted portion and into the closed portion to become impositively trapped therein.

The material of the channel shaped member is preferably such that it can receive and permanently retain markings identifying certain ones of the slots in the outer wall portion.

An individualized flossing mouthpiece for simultaneously flossing a plurality of spaces between a person's adjacent pairs of teeth comprises an individualizable flossing mouthpiece as just described bearing visible permanent non-toxic markings identifying those slots in the outer wall portion corresponding to the locations of the edges of the person's teeth when the person's teeth are in the gap, the so identified ones of the slots being less than all of the slots in the outer wall portion.

An individualized flossing mouthpiece assembly comprises an individualizable flossing mouthpiece as just described and a piece of dental floss that is impositively trapped in those slots in said outer wall portion which bear the markings and in those slots in the inner wall portion corresponding to the slots in the outer wall portion bearing the markings, with the dental floss passing through a first marking bearing slot in the outer wall portion, directly across the gap to and through a slot in the inner wall portion, along the inner wall portion to and through another slot in the inner wall portion directly across the gap from a second marking bearing slot in the outer wall portion and directly across the gap to and through said second marking bearing slot and so forth. Less than all the slots are occupied by the floss, and less than all the slots in the outer wall portion bear markings.

The invention also provides a method of preparing an individualized flossing mouthpiece assembly for use by a person in simultaneously flossing a plurality of spaces between the person's teeth. This method is performed with the aid of a piece of dental floss and an individualized flossing mouthpiece, which is a channel shaped member including an outer wall portion and an inner wall portion. The outer and inner wall portions have free edges with a gap between the wall portions. The gap is sized and shaped to receive a set of teeth loosely therein. The outer wall portion and the inner wall portion are provided, respectively, with outer and inner series of closely spaced slots in open communication with the free edges. The method comprises the steps of placing the individualized flossing mouthpiece in the person's mouth with the person's upper or lower teeth in the gap, placing permanent non-toxic markings on the outer wall portion to identify locations of the slots in the outer wall portion corresponding to spaces between adjacent pairs of the person's teeth, removing the mouthpiece from the person's mouth and thereafter inserting the dental floss into those slots with the markings, those slots in the inner wall portion directly opposite those slots with the markings, across the gap and along the outer wall portion and the inner wall portion.

The invention further provides a method of simultaneously flossing a plurality of spaces between a person's teeth. This method is performed with the aid of an individualized flossing mouthpiece assembly. As just described, the individualized flossing mouthpiece assembly includes a flossing mouthpiece having a gap and a piece of dental floss strung tautly across the gap at spaced locations corresponding to the spaces between adjacent pairs of the person's teeth. The method comprises the steps of placing the individualized flossing mouthpiece assembly in the person's mouth with the person's teeth in the gap and with the dental floss in the spaces between the person's teeth, moving the assembly to cause the dental floss to move back and forth in the spaces and removing the assembly from the person's mouth.

DESCRIPTION OF THE INVENTION

Figure 1:
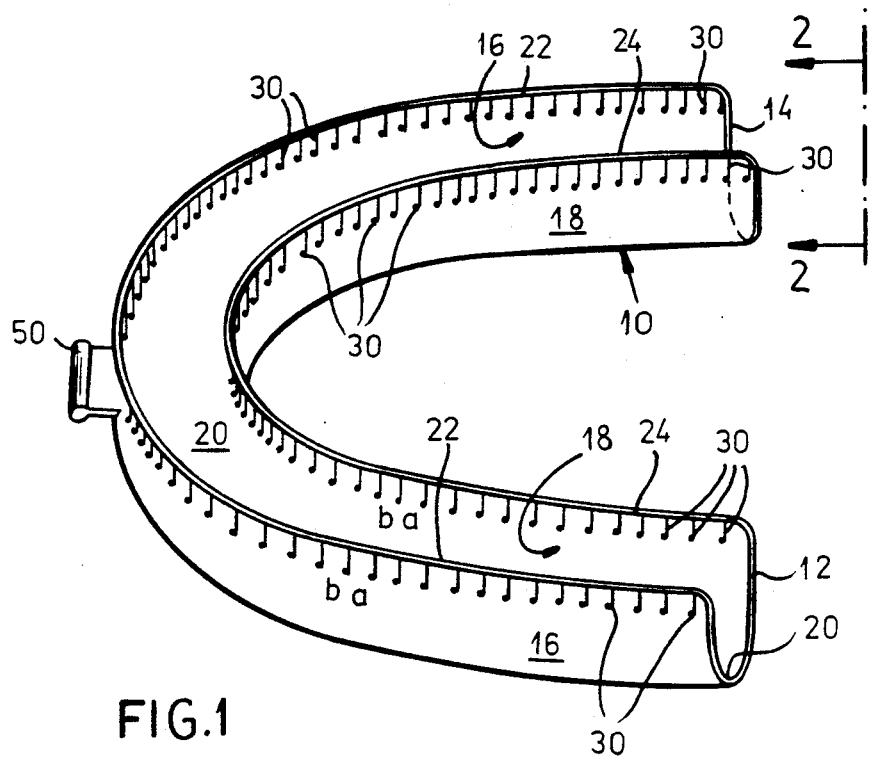
FIG. 1 is a perspective view of an individualizable flossing mouthpiece that is a preferred embodiment of the invention.
Figure 2:
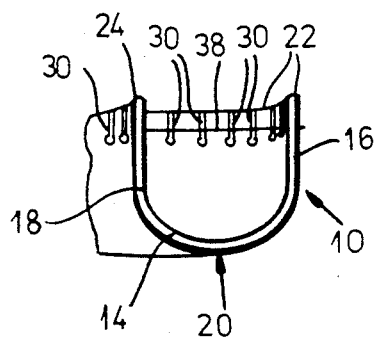
FIG. 2 is a fragmentary view taken on line 2—2 of FIG. 1.

FIG. 1 shows an individualizable flossing mouthpiece 10 that is a preferred embodiment of the invention. Mouthpiece 10, which is of suitable preferably transparent material and of one-piece construction, is a channel shaped member of substantially constant wall thickness add extending from a first open end 12 to a second open end 14. Ends 12 and 14 face in generally the same direction. The channel shaped member that is mouthpiece 10 includes an outer wall portion 16, an inner wall portion 18 and a web portion 20 joining wall portions 16 and 18. Web portion 20 is as shown imperforate but is not necessarily so. Wall portions 16 and 18 and web portion 20 extend from end 12 to end 14 and wall portions 16 and 18 are everywhere spaced substantially the same distance apart. Wall portions 16 and 18 have a gap therebetween and free edges 22 and 24, respectively, to which portions 16 and 18 extend from web portion 20. As will be appreciated particularly from FIG. 1, wall portions 16 and 18 are such that mouthpiece 10 is generally C-shaped in plan view.

Figure 3:
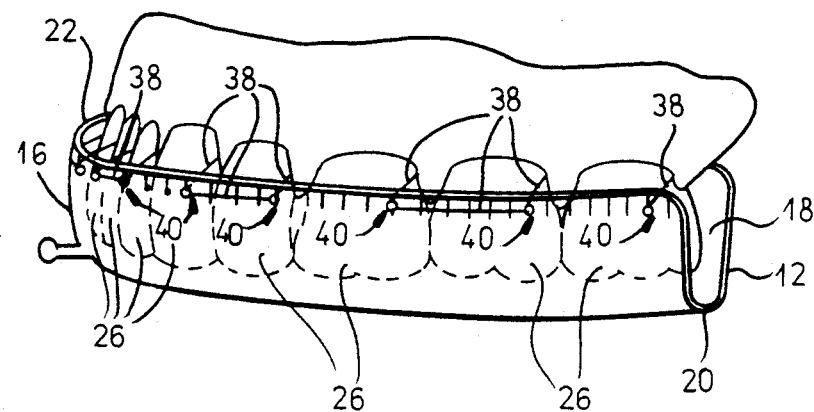
FIG. 3 is substantially a side view of an individualized flossing assembly comprising dental floss and an individualized flossing mouthpiece made from the individualizable flossing mouthpiece of FIG. 1, the individualized flossing assembly being shown in flossing relationship with a set of upper teeth.

In any event, the channel shaped member that is mouthpiece 10 is sized and shaped to receive somewhat loosely therein, in the gap between wall portions 16 and 18, a set of lower teeth or a set of upper teeth, the latter being indicated at 26 in FIG. 3.

Each of outer wall portion 16 and inner wall portion 18 is provided with a series of parallel, closely spaced slots 30. Slots 30 in outer wall portion 16 are in open communication with free edge 22 and slots 30 in inner wall portion 18 are in open communication with free edge 24. Slots 30 in each of wall portions 16 and 18 include two end slots 30, one closely adjacent to open end 12 and the other closely adjacent to open end 14. The spacing of slots 30 may be constant or varied but in any event is less than the width of an average tooth.

Preferably each slot 30 in outer wall portion 16 is provided on the outer surface of wall portion with a unique identifying label. Such labels may be letters, such as a, b, c, etc., as seen in FIG. 1. Preferably, too, each slot 30 in inner wall portion 18 is provided with an identifying label that is the same as the label that is applied to corresponding slot 30 in outer wall portion 16. As further seen in FIG. 1, that slot 30 in inner wall portion 18 that is directly opposite that slot 30 in outer wall portion 16 that bears label a also bears label a, that slot 30 in inner wall portion 18 that is directly opposite that slot 30 in outer wall portion that bears label b also bears label b, that slot 30 in inner wall portion 18 that is directly opposite that slot 30 in outer wall portion 16 that bears label c also bears label c, etc. As shown, labels a, b, c, etc., on inner wall portion 18 appear on the outer surface thereof, i.e. the surface thereof facing toward outer wall portion 16, but labels a, b, c, etc., on inner wall portion 18 could be on the inner surface thereof, i.e. the surface thereof facing away from outer wall portion 18. Or, as will be described, labels such as a, b, c, etc. could be omitted altogether.

Figure 4:
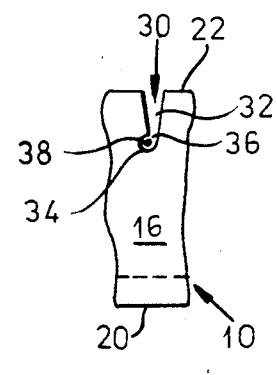
FIG. 4 is an enlarged fragmentary view of a detail of the flossing assembly showing dental floss held in assembled relationship with the mouthpiece.

FIG. 4 shows an enlarged detail of any slot 30. It will be assumed that FIG. 4 shows a slot 30 in outer wall portion 16, but it is to be understood that slots 30 in inner wall portion 18 are exactly the same as that slot 30 shown in FIG. 4. With further reference to FIG. 4, it will be seen that slot 30 has a V-shaped portion 32 that is widest at its location of open communication with free edge 22 and is generally perpendicular to free edge 22 and also that slot 30 has a closed portion 34 in open communication with the end of V-shaped portion 32 remote from free edge 22. Closed portion 34 is generally cylindrical and is slightly offset from the plane of symmetry of its associated V-shaped portion 32, so as to provide a constricted portion 36 joining V-shaped portion 32 and closed portion 34.

In result, a piece of dental floss 38 can be introduced into V-shaped portion 32 and moved therein to and beyond constricted portion 36 and into closed portion 34. The width of constricted portion 36 is less than the diameter of dental floss 38, which is thereby radially compressed while it passes through constricted portion 36. After floss 38 passes through constricted portion 36 it expands radially in closed portion 34, where floss 38 becomes impositively trapped.

To prepare an individualized flossing mouthpiece assembly from mouthpiece 10 for use by a particular person, one first transforms individualizable flossing mouthpiece 10 into an individualized flossing mouthpiece. To that end, mouthpiece 10 is placed in the person's mouth with the person's upper (for example) tee 26 between outer and inner wall portions 16 and 18, respectively, as shown in FIG. 3. An operator, such as a dental hygienist, then identifies those slots 30 in outer wall portion 16 corresponding to locations of adjacent edges of the person's teeth 26 and makes a record of those slots 30 so identified. The record could be made by placing on the outer surface of outer wall portion 16 permanent non-toxic markings, some of which are indicated at 40, on those slots 30 so identified, or by making a list of those pre-applied labels a, b, c, etc. corresponding to those slots 30 so identified. This completes the transformation of individualizable mouthpiece 10 to individualized flossing mouthpiece 10.

Mouthpiece 10 is then removed from the person's mouth and strung with dental floss 38, which is knotted at one end, and pushed alternately into those slots 30 so identified in outer wall portion 16 and into those slots 30 in inner wall portion 18 directly opposite those slots 30 with the markings 40 thereon in outer wall portion 16. Floss 38 is then pulled taut and knotted at the other end. The use of labels a, b, c, etc. on wall portions 16 and 18 facilitates finding the proper slots 30 in inner wall portion 18.

Dental floss 38, now installed in individualized fashion in flossing mouthpiece 10, is a single piece of dental floss passing alternately through a slot 30 so identified in outer wall portion 16, tautly across the gap between portions 16 and 18, through an appropriate slot 30 in inner wall portion 18, along inner wall portion 18 to and through the next appropriate slot 30 in inner wall portion 18, across the gap to and through the next slot 30 so identified in outer wall portion 16, and so on, until all slots 30 so identified have been used.

The result of the foregoing is an individualized flossing mouthpiece assembly comprising mouthpiece 10 and taut floss 38, which assembly can then be placed in the person's mouth and pushed to insert floss 38 into the spaces between adjacent pairs of teeth 26. Flossing is then performed utilizing a combination of left and right and forward and backward movements of mouthpiece 10. Such movements are facilitated by knob 50 (FIG. 1) that projects outwardly from outer wall portion 16 at the longitudinal or arcuate center thereof. Knob 50 can be grasped between the person's thumb and index finger, to effectuate flossing movement.

Spent floss 38 can be easily replaced using the previously made permanent markings 40.

It is contemplated that a second individualized flossing mouthpiece assembly would be prepared for flossing the same person's lower teeth, in the manner already described.

It is also contemplated that individualizable flossing mouthpiece 10 would have to be provided in a plurality of sizes and shapes.

It is evident that the invention attains the foregoing objects and advantages, among others.

The disclosed details are exemplary only and are not to be taken as limitations on the invention except as those details may be included in the appended claims.

What is claimed is:

1. An individualizable flossing mouthpiece for use in simultaneously flossing a plurality of spaces between adjacent pairs of teeth, said mouthpiece being a channel shaped member including an outer wall portion, an inner wall portion and a web portion joining said wall portions, said wall portions having a gap therebetween and extending from said web portion to free edges and being curved in plan view, said mouthpiece being sized and shaped to receive a set of teeth loosely in said gap, said outer wall portion and said inner wall portion being provided respectively with outer and inner series of identical closely spaced slots adapted to receive dental floss therein, each said slot of said outer series having an open end in open communication with said free edge of said outer wall portion and each said slot of said inner series having an open end in open communication with said free edge of said inner wall portion, the distance between adjacent ones of said slots of said outer and inner series being less than the width of an average tooth.

2. An individualizable flossing mouthpiece according to claim 1 wherein said wall portions are arcuate, such that said mouthpiece is generally C-shaped in plan view.

3. An individualizable flossing mouthpiece according to claim 2 further comprising a knob projecting outwardly from said outer wall portion at the longitudinal center thereof.

4. An individualizable flossing mouthpiece according to claim 2 wherein said channel shaped member has first and second open ends facing generally in the same direction.

5. An individualizable flossing mouthpiece according to claim 1 wherein each said slot has a V-shaped portion widest at said open end of said slot and narrowest at a location remote from said open end and a closed portion in open communication with said V-shaped portion at its said narrowest location.

6. An individualizable flossing mouthpiece according to claim 5 wherein said closed portion of each said slot is generally cylindrical and is offset from a plane of symmetry of its associated said V-shaped portion, so as to provide a constricted portion joining said V-shaped portion and said closed portion.

7. An individualizable flossing mouthpiece according to claim 6 wherein dental floss introduced into said V-shaped portion of any said slot can be moved therein to and beyond said constricted portion and into said closed portion to become positively trapped therein.

8. An individualizable flossing mouthpiece according to claim 1 wherein the material of said channel shaped member is such that it can receive and permanently retain markings identifying certain ones of said slots in said outer wall portion.

9. An individualized flossing mouthpiece for simultaneously flossing a plurality of spaces between a person's adjacent pairs of teeth, comprising an individualizable flossing mouthpiece according to claim 8 and an identification of those said slots in said outer wall portion corresponding to the locations of the edges of the person's teeth when the person's teeth are in said gap, the so identified ones of said slots being less than all of said slots in said outer wall portion.

10. An individualized flossing mouthpiece according to claim 9 wherein said identification is provided by visible permanent non-toxic markings applied to the pertinent ones of said slots in said outer wall portion.

11. An individualizable flossing mouthpiece according to claim 1 wherein each said slot in said outer wall portion is provided on the outer surface of said outer wall portion with a unique identifying label.

12. An individualizable flossing mouthpiece according to claim 11 wherein each said slot in said inner wall portion is provided with an identifying label that is the same as said label that is applied to the corresponding said slot in said outer wall portion.

13. An individualized flossing mouthpiece for simultaneously flossing a plurality of spaces between a person's adjacent pairs of teeth, comprising an individualizable flossing mouthpiece according to claim 12 and an identification of said unique identifying labels of those of said slots in said outer wall portion corresponding to the locations of the edges of the person's teeth when the person's teeth are in said gap, the so identified ones of said slots being less than all of said slots in said outer wall portion.

14. An individualized flossing mouthpiece for simultaneously flossing a plurality of spaces between a person's adjacent pairs of teeth, comprising an individualizable flossing mouthpiece according to claim 11 and an identification of said unique identifying labels of those of said slots in said outer wall portion corresponding to the locations of the edges of the person's teeth when the person's teeth are in said gap, the so identified ones of said slots being less than all of said slots in said outer wall portion.

15. An individualized flossing mouthpiece assembly for simultaneously flossing a plurality of spaces between a person's adjacent pairs of teeth, said assembly comprising dental floss and a flossing mouthpiece which is a channel member including an outer wall portion, an inner wall portion and a web portion joining said wall portions, said wall portions having a gap therebetween and extending from said web portion to free edges and being curved in plan view, said mouthpiece being sized and shaped to receive a set of teeth loosely in said gap, said outer wall portion and said inner wall portion being provided respectively with outer and inner series of identical closely spaced slots adapted to receive dental floss therein, each said slot of said outer series having an open end in open communication with said free edge of said outer wall portion and each said slot of said inner series having an open end in open communication with said free edge of said inner wall portion, the distance between adjacent ones of said slots of said outer and inner series being less than the width of an average tooth, said dental floss passing through a first slot in said outer wall portion, directly across said gap to and through a first said slot in said inner wall portion and through a second slot in said outer wall portion, directly across said gap to and through a second slot in said inner wall portion, said first and second slots in said outer wall portion corresponding to the locations of spaces between a plurality of the person's teeth.

16. An individualized flossing mouthpiece assembly according to claim 15 wherein between said first and second slots there are additional slots in said outer wall portion, which said additional slots are unoccupied.

17. A method of preparing an individualized flossing mouthpiece assembly for use by a person in simultaneously flossing a plurality of spaces between the person's teeth, said method performed with the aid of a piece of dental floss and an individualizable flossing mouthpiece, which is a channel shaped member including an outer wall portion and an inner wall portion, said outer and inner wall portions having free edges, a gap between said wall portions and sized and shaped to receive a set of teeth loosely in said gap, and said outer wall portion and said inner wall portion being provided, respectively, with outer and inner series of closely spaced slots in open communication with said free edges, said method comprising the steps of placing said individualizable flossing mouthpiece in the person's mouth with the person's upper or lower teeth in the gap, identifying locations of the slots in said outer wall portion corresponding to spaces between adjacent pairs of the person's teeth, removing the mouthpiece from the person's mouth and thereafter inserting said dental floss into those slots so identified those slots in the inner wall portion directly opposite those slots so identified, across the gap and along the outer wall portion and the inner wall portion.

18. A method of simultaneously flossing a plurality of spaces between a person's teeth, said method performed with the aid of an individualized flossing mouthpiece assembly including a flossing mouthpiece having a gap and a piece of dental floss strung tautly across the gap at spaced locations corresponding to the spaces between adjacent pairs of the person's teeth, said method comprising the steps of placing the flossing mouthpiece assembly in the person's mouth with the person's teeth in the gap, with the dental floss in the spaces between the person's teeth, moving the flossing mouthpiece assembly to cause the dental floss to move back and forth in the spaces and removing the flossing mouthpiece from the person's mouth.

* * * * *